(12) United States Patent
Szu

(10) Patent No.: US 7,355,182 B2
(45) Date of Patent: Apr. 8, 2008

(54) INFRARED MULTI-SPECTRAL CAMERA AND PROCESS OF USING INFRARED MULTI-SPECTRAL CAMERA

(76) Inventor: Harold Szu, 12801Missiomwood Way, Potomac, MD (US) 20854

( * ) Notice: Subject to any disclaimer, the term of this patent is extended or adjusted under 35 U.S.C. 154(b) by 148 days.

(21) Appl. No.: 11/245,946

(22) Filed: Oct. 6, 2005

(65) Prior Publication Data

US 2006/0097176 A1    May 11, 2006

Related U.S. Application Data

(60) Provisional application No. 60/616,800, filed on Oct. 6, 2004.

(51) Int. Cl.
*G01T 1/24* (2006.01)
(52) U.S. Cl. .................................. 250/370.08
(58) Field of Classification Search ............ 250/370.08
See application file for complete search history.

(56) References Cited

U.S. PATENT DOCUMENTS

| | | | |
|---|---|---|---|
| 6,280,677 B1 * | 8/2001 | Yakobson | 264/430 |
| 2004/0119020 A1 * | 6/2004 | Bodkin | 250/353 |
| 2005/0285038 A1 * | 12/2005 | Frangioni | 250/330 |

\* cited by examiner

*Primary Examiner*—David Porta
*Assistant Examiner*—Mark R Gaworecki
(74) *Attorney, Agent, or Firm*—IP Strategies

(57) ABSTRACT

A process of performing a medical test includes taking multi-spectral images of an area of interest of a patient. The patient can be a human being or an animal, and can be known to be healthy or known to have health issues or problems. A multi-spectral camera includes a long-infrared charge-coupled device, a mid-infrared detector array, and a control device that synchronizes operation of the charge-coupled device and the detector array. The mid-infrared detector array can include carbon nanotubes. The carbon nanotubes can be detector elements. For example, the carbon nanotubes can be tuned-bandgap carbon nanotubes. Each pixel of resolution of the detector array can include a balanced Wheatstone bridge circuit including one of the tuned-bandgap carbon nanotubes. Adjacent pixels of the detector array can be arranged for orthogonal polarization.

76 Claims, 8 Drawing Sheets
(6 of 8 Drawing Sheet(s) Filed in Color)

INFRARED MULTI-SPECTRAL CAMERA AND PROCESS OF USING INFRARED MULTI-SPECTRAL CAMERA

CROSS-REFERENCE TO RELATED APPLICATION

This is related to and claims priority from U.S. Provisional Patent Application Ser. No. 60/616,800, which was filed on Oct. 6, 2004.

FIELD OF THE INVENTION

The present invention relates to cameras, particularly cameras that provide thermal images for analysis.

BACKGROUND OF THE INVENTION

Multi-spectral cameras have long been used for many different applications. Multi-spectral camera systems typically include software for camera control, image acquisition, and image analysis, so that the imaged object can be used for some diagnostic purpose. For example, such images can be used for airborne reconnaissance and terrestrial observation, environmental characterization, and military applications such as target acquisition, camouflage penetration, and surveillance. These cameras are cryogenic, that is, they use liquid nitrogen or other coolants to reduce thermal noise present in the images so that the signal-to-noise ratio is adequate. Thus, these apparatus are not suitable for use as consumer devices.

Night-vision long infrared cameras are well-known, and are sold commercially by a number of companies. These conventional cameras are non-cryogenic cameras, that is, they are built without liquid nitrogen or other coolants. These cameras provide a visible image under low-light conditions, but they are blind with respect to spectrum. This limits conventional cameras such that they cannot be effectively used for certain applications. For example, conventional cameras cannot be used to quantitatively determine early tumor development. Rather, a middle infrared spectrum camera must be used for this application and, due to low signal-to-noise ratio of the resulting image, one must use liquid nitrogen to cool down the camera detector backplane.

It would be advantageous to provide a multi-spectral camera that is commercially available and preferably features a non-cryogenic design. It also would be advantageous to provide a process by which such a camera can be used to test for and diagnose medical conditions, such as cancer, for use in human and veterinary medicine. Understanding of genotype & phenotype of cancers had led to advances in diagnoses and treatments of cancer; nevertheless, the battle against cancer remained to be a major concern; for example, in the U.S. alone over 200,000 women and 1,500 men are diagnosed with malignant breast tumors every year. It would be advantageous to provide a convenient and reliable screening methodology with inexpensive telemedicine decision aids in households, to complement a public awareness in healthy living style.

BRIEF DESCRIPTION OF THE INVENTION

Several active imaging modalities have already been adopted in hospitals and laboratories using, for example, targeted radiation spectrum of radio waves in f-NMI, X-rays for mammograms, and gamma-rays for PET. Modern satellite imaging & smart military ATR technology passively receive radiation from targets and are non-intrusive. Less expensive versions for ground operation can be utilized for household or lab purposes. Traditional thermal imaging known as the thermograms can be improved over the conventional practice of using one IR spectrum-integrated camera to take two pictures of a patient sitting in a dark cold room a few minutes apart, which practiced with a mixed reputation for decades. Because high-precision satellite-grade cameras operating cryogenically in seven spectral bands from visible to IR are capable of detecting a hidden tank hot engine in the desert over thousand miles above the earth, a less expensive and portable versions of IR two-color CCD cameras (mid IR band from 3 to 5 microns wavelengths and the long IR band from 8 to 12 microns in terms of semi-conductor bang-gap material), having a reduced size of about 512×512 pixels operated at a minimum resolvable temperature difference (MRTD) of about 0.02 to 0.1 degree Kelvin can be used for close-up imaging of patients by household caretakers. Since such non-intrusive imaging screening methodology is passive and therefore non-specific, a NIH/NIBIB benchmark would require anyone to conduct an experiment of human subjects of 100,000 healthy but risky population: (i) Institute Review Board (IRB), (ii) Consent Patient Form (CPF) & (iii) tabulated results, in terms of the Receiver Operation Characteristics (ROC), of which a control study for 0.1% disease rate over five years might result in 100 sick patients with probability of detection (PD) versus False Alarm/Negative Rate (FAR). These requirements were beyond available resources and commitment level, so instead, a reverse approach was chosen. Rather than taking a large group of healthy but high-risk volunteers, a volunteer group of sick patients was used, in collaboration with Thermal Scan Inc. U.S., and Pontifical Lateral University at Vatican City of Rome, Italy, and nearby hospitals. The uncertainty of initial search was avoided and the sick patients were tracked under chemotherapy using IR two-color cameras. Vatican involvement was beneficial because passive and non-intrusive screening for breast tumors was based on (i) a ten-fold higher risk factor for nulliperous women, according to recent epidemiology studies in Singapore and (ii) a smart ATR algorithm was demonstrated by a pair of satellite-grade spectral-grams in tracking the Wien spectral peak displacement law over time. A sequence of time-order snapshots documented that successful recovery history in a time-contract-animated video. Getting better is not necessarily equivalent to getting worse physiologically, even when identical cameras and a smart algorithm are used. Moreover, such a new generation of non-mercury-contact spectrum thermometer can be available for general purpose usage, for those who cannot frequently take expensive and intrusive diagnostic modalities. A physics model of two IR color spectral-grams is provided, and a brief overview of active imaging and second generation anti-angiogenesis drugs is provided for the convenience of interdisciplinary studies.

To facilitate interdisciplinary collaboration, a simple but representative overview of various imaging modalities and cancer drugs usages are provided. According to oncological practice, an excessive new blood vessel can be generated, via Vascular Endothelial Growth Factor (VEGF) & other molecular signaling receptors, to supply the metabolic needs of oxygen, glucose, and other nutrition to a rapid-growth malignant tumor site, known as angiogenic blood vessel generation, an effect common to the metastasis of most malignant tumors. For example, ionizing UV & IR radiation of sunburn-damaged ATR & ATM of cells causes gene defects at CHK1 & CHK2, respectively. On the other hand, BRCA2 gene-deficient cells caused instability of chromosomes due to spindle abnormal cytokines. A common mechanism of cancer was suspected to be DNA reproduction without apoptosis programming of death. Advances with molecule-tagged cellular imaging had improved doctors' ability to diagnose and treat patients: (i) functional-Nuclear Magnetic Imaging (f-NMI) imaged the blood "hemodynamics" following the metabolic need of oxygen, of which a new algorithm improved higher-order spectral correlation when spectral lines increased the resolution under an increased magnetic field & cost of f-NMI device; (ii) in addition to oxygen, glucose is also required conjugated with an unstable isotope capable of decaying into a Positron, which is annihilated locally inside a patient with an electron within sub-mm mean free path resolution, Emitting gamma rays, 0.5 MeV, in two opposite directions which provide a direct internal radiation projection imaging Tomogram in the so-called PET for the imaging sugar "glucodynamics"; (iii) red-light tagged florescence molecular imaged in contrast with the opposite green-light-tagged florescence; (iv) an improved safety margin of X-ray dosage of mammograms. These high-energy radiation image modalities are too sophisticated costly for typical household ownership and use. Current passive IR spectral-grams study augmented these modalities, as double-blind tests when determined to be successful, could be potential supplements at labs and in homes.

Because current reverse or backward study to track the progress of chemotherapy treatments of already-sick patients involved some new anti-angiogenesis cancer drugs, they were briefly reviewed under "starving tumors of blood" with drug and chemotherapy for the convenience of cross-disciplinary imaging experts. For instance, FDA approved Genetech's anti-body "Avastin", injected to augment the chemotherapy, to extend a patient's life from 6 to 11 months. Some of new anti-angiogenesis drugs are already in Phase III trial and could be made available for treatments, which, rather than being injected, are small enough to swallow as pills and made more than just "starving tumors of blood", but to aim at multiple molecular targets for inhibition or competition. Bayer's Sorafenib, discovered 4 years ago for kidney cancer, can inhibit tyrosine kinases: Raf and other receptors of VEGF. Another second generation drug, SUGEN's Sutant, was discovered a year earlier and was recently acquired by Pfizer, proved its inhibition of the protein produced by KIT oncogene of stomach cancer GIST patients, and demonstrated furthermore with some positive affects on breast cancer and other cancers. Moreover, passive IR spectral-gram tracking might help monitor nano-scale targeted-drug delivery systems which had made significant promises, including in-situ laser burning of cancer cells having rich folate receptors using the vitamin-folate-guided carbon nanotube for IR-absorption generating rapidly heat killing cancer cells without harming healthy tissue. All these new drugs and nano-technology were timely for a new epidemiology study revealing an elevated increase of kidney cancer patients on the east coast of the U.S. Another large category of cancer is breast cancer, which has struck over 200,000 in 2005 so far, with a mortality rate of about 18.8%. Breast cancer deaths are less than those attributed to lung cancer, which number over 80,000 per year at a 85% mortality rate. Nevertheless, a 0.1% of risk of Ductile Carcinoma In Situ (DCIS) increased to 1% for nulliparous mothers without children according to Singapore public health statistics & biannual reports of epidemiologist Frank Speizer et al.

According to an aspect of the invention, a process of performing a medical test includes taking multi-spectral images of an area of interest of a patient. The patient can be a human being or an animal, and can be known to be healthy or known to have health issues or problems.

Taking multi-spectral images can include taking substantially simultaneous images of the area of interest using a plurality of cameras, wherein each of the cameras provides an image in respective different spectra. The cameras can be, for example, infrared cameras, and the spectra can be infrared spectra. The plurality of cameras can be, for example, two cameras.

Alternatively, taking multispectral images can include taking images using a multiple-spectrum camera. For example, the multiple-spectrum camera can be a dual-spectrum camera, such as a dual-spectrum infrared camera. The camera can include any two of a long-infrared wavelength detector, a mid-infrared wavelength detector, and a short-infrared wavelength detector. Preferably, the dual-spectrum infrared camera includes a long-infrared wavelength detector and a mid-infrared wavelength detector. The mid-infrared wavelength detector can include a detector array having carbon nanotubes. The carbon nanotubes can be detector elements. For example, the carbon nanotubes can be tuned-bandgap carbon nanotubes. Each pixel of resolution of the detector array can include a balanced Wheatstone bridge circuit including one of the tuned-bandgap carbon nanotubes.

The camera can be cooled by electrical dissipation. Alternatively, the camera can be cooled by refrigeration. For example, the camera can include a backplane, which can be refrigerated. As another alternative, the multiple-spectrum camera can be cryogenically cooled, such as by using liquid nitrogen as a coolant.

A process of performing a medical diagnosis can include performing a medical test as described above, comparing the images to spectrograms of subjects having a known health issue, and diagnosing a health status of the patient based on a correlation of the images to the spectrograms.

A process of performing a medical prognosis can include performing a medical test as described above, wherein the patient has a known health issue of a particular type, comparing the images to spectrograms of subjects having the known health issue of the particular type, and providing a prognosis for the patient based on a correlation of the images to the spectrograms.

According to another aspect of the invention, a multi-spectral camera includes a long-infrared charge-coupled device, a mid-infrared detector array, and a control device that synchronizes operation of the charge-coupled device and the detector array. The mid-infrared detector array can include carbon nanotubes. The carbon nanotubes can be detector elements. For example, the carbon nanotubes can be tuned-bandgap carbon nanotubes. Each pixel of resolution of the detector array can include a balanced Wheatstone bridge circuit including one of the tuned-bandgap carbon nanotubes. Adjacent pixels of the detector array can be arranged for orthogonal polarization.

The multi-spectral camera can also include conductive members that cool the detector array by dissipation. Alternatively, the camera can include a refrigeration element that cools the detector array. As another alternative, the camera can include a cryogenic cooling element that cools the detector array. For example, the cryogenic cooling element can use liquid nitrogen as a coolant.

Preferably, the charge-coupled device and the detector array are co-axially aligned.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

High-precision spy cameras on board satellites located thousands of miles away can precisely detect and image the hot engine of a car or tank, or a missile plume, with the help of aided target recognition (ATR) techniques using multiple spectrogram features of a spontaneous thermal emission. Likewise, by transferring such military technology "from tank to tumor", we can discover a hidden ductile carcinoma in-situ (DCIS) of a patient in a close-up setting according to the angiogenesis heating effect of new blood vessels working to feed a fast-growing malignant tumor.

Figure 1:
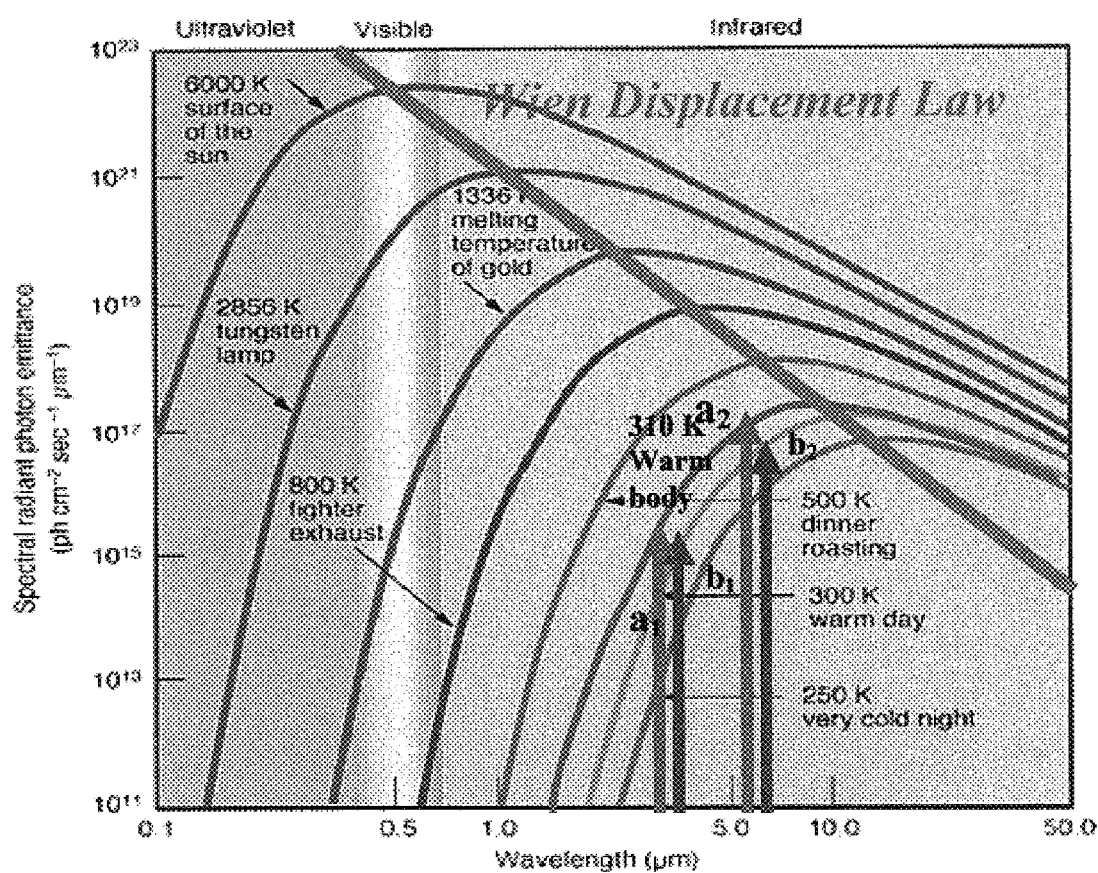
FIG. 1 is a graph illustrating Wien's displacement rule of Planck blackbody cavity radiations.

As shown in FIG. 1, Wien's displacement rule of Planck blackbody cavity radiations is a linear law in terms of the log-log plot of the peak radiation intensity versus the wavelengths, of which Einstein photon dispersion is a special case in a vacuum at the slope m=1. Spectrograms features abnormal $\vec{a}=(a_1, a_2)$; body $\vec{b}=(b_1, b_2)$ based on the Planck Radiation Spectrum Distribution whose mean values of mid IR band (3-5 micron) and long IR band (8-12 micron) wavelength.

Almost all portions of the electromagnetic wave spectrum have previously been explored for medical applications, for example, blackbody radiation spectrum (FIG. 1); a short wavelength at gamma ray: PET; and at X-rays: mammogram; and radio waves: f-NMI. All utilize some man-made radiation sources to actively probe patients with sophisticated equipment and imaging processing algorithms. A notable exception is passive thermographs, which utilize a single thermal camera to image a patient's self-emitted heat radiation in a dark cold room, similar to colorless night vision, and subsequently exam the patient again for any remnant hot spot after being cool down, as shown, for example, in FIG. 2. In this conventional practice, two recordings per session are necessary: the first recording is made soon after the patient undresses, and the second is made after some duration has passed. This procedure requires an embarrassing wait in a chilly room (typically cooled lower than 21° C.). The first image (left) was taken within 1 minute after the patient undressed while the second one was taken 10 minutes later, during which time a normal pair of breasts became blue cold (right).

Figure 3:
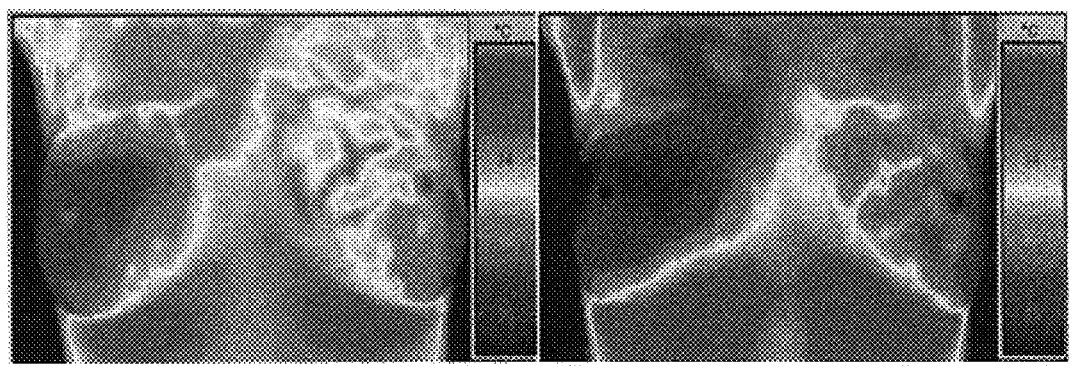
FIG. 3 shows a conventional breast cancer diagnosis spectrogram for a patient with breast cancer.

FIG. 3 shows that in this example the right breast continues to emanate heat radiation in the cold dark room even after the average body temperature decreased, for example, by immersion of the patient's hands in ice water. The extra heat could be an indication of active blood vessels generated to feed a malignant tumor, known as the angiogenesis effect. However, conventional non-intrusive and affordable thermographs can only lead a medical professional to speculate as to the cause behind those remnant hot spots. According to the present invention, the single camera is replaced by two cameras in recording the temporal increase, with the dual IR spectrograms ratio to be the salient invariant feature of malignance.

Figure 4:
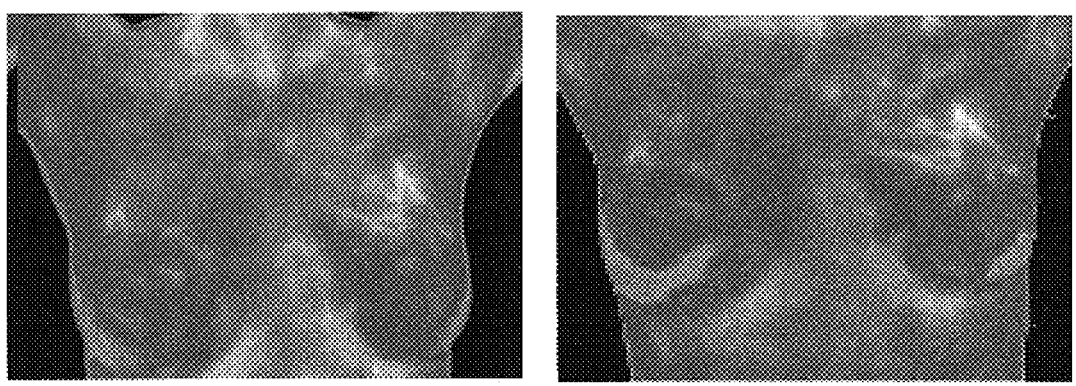
FIG. 4 shows a breast cancer diagnosis spectrogram according to the present invention.

The approach of the present invention is to improve the precision of two cameras and to derive from the equilibrium thermodynamics principle the invariant feature to modify its pattern recognition by unsupervised ATR, or unlabelled data classifier by Dude & Hart definition, as follows. A starting point is the feasibility of a pair of satellite-grade cameras taking dual IR spectrograms of patients under anti-angiogenesis treatments. A volunteer patient is exemplified in FIG. 4, who is tested according to the process of the invention and diagnosed subsequently to be DCIS zero stage in her right breast nipple. According to this two-camera multispectral infrared breast image (left mid-IR and right long-IR), only one instantaneous and simultaneous recording per session was sufficient for the unsupervised classification of sub-pixel super-resolution algorithm. This non-intrusive, dark-room private, and passive imaging permits one with conveniently tracking of the hemodynamics phase transition to follow the angiogenesis of the breast pre-cancer tumor development for a potential telemedicine decision of early pre-cancer intervention. Several passive and non-intrusive spectrogram snapshots are animated into a time-reversible video, and playing backward, give virtual cancer-development dynamics that might not be accurate but the demonstrated tracking capability justifies a direct screen study for pre-cancer detection.

According to Fourier's conduction law, heat always flows from a hotter inside region to a colder ambient outside region to reach an equilibrium condition no matter how deep the heat sources are hidden. In addition to different degrees of angiogenesis activity, the differences in the depths can also result in different total image intensity and image spot size. Thus, instead of dealing with the unpredictable total intensity value, it is advantageous to explore an invariant feature of the dual IR spectrograms ratio. It is assumed that an unknown mixture of benign or malignant DCIS tumors exist in an arbitrary metastasis activity state. They might be located at an unknown depth within normal breast body tissue. According to Planck's blackbody radiation law, a healthy human body emits invisible IR radiation less efficiently than does an ideal blackbody oven kept at a constant temperature $T_o=37°$ C.$+273°$ K with a radiation leakage pinhole. We are brown bodies, so to speak, producing dual IR spectrograms: $\vec{b}=(b_1, b_2)$ normalized at an equivalent heat source $s'_2$, as shown in FIG. 1. A malignant tumor of strength $s'_1$ can radiate as an equivalent blackbody at a slightly elevated temperature $T_o=37°$ C.$+\Delta+273°$ K, whose mean values of dual spectrograms results in an abnormal feature vector, $\hat{a}=(a_1, a_2)$, with reference again to FIG. 1. Assuming two IR spectral cameras, perfectly registered & calibrated, we can take two spectral images at time t, resulting in two spectrograms. The image gray scale values at the corresponding pixel p are denoted as the spectral image vector: $\vec{X}'_p(t) \equiv (x'_1(t), x'_2(t))^T$, where the prime indicates the physical unit of spectrograms in watts per cm² per pixel. According to the thermal physics model, we assume a weakly linear mixture of two isotropic sources that generates an unknown mixture of IR dual spectrograms:

$$\vec{X}'_p(t) = [A'_p(t)]\vec{S}'_p(t); [A'_p(t)] \equiv C'_p(t)\begin{bmatrix} a'_1 & b'_1 \\ a'_2 & b'_2 \end{bmatrix}; \quad (1)$$

$$C'_p(t) = \int_{\lambda_1}^{\lambda_2} \iiint_{tumor} \exp\left(\frac{-|\vec{z}|}{c'_p(\lambda, \vec{z})}\right) R(\lambda, T(t)) d^3 z \, d\lambda,$$

where the Planck emission distribution R is integrated over the long IR regime $\lambda_2$ to the mid IR band $\lambda_1$. These spectral intensities suffer diffusion and conduction loss with an exponential decay function $c'_p(\lambda, \vec{z})$ of the wavelength and the medium property sampled through by the radiation source at the depth $|\vec{z}|$. Equating the conservation law of energy, $|\vec{X}'_p| \equiv \sqrt{x'_1{}^2 + x'_2{}^2} \equiv C'_p(s'_1 + s'_2)$, dimensionless spectrograms are introduced without the prime $\vec{X}_p \equiv \vec{X}'_p(x'_1{}^2 + x'_2{}^2)^{-1/2}$ and normalized sources $\vec{S}_p \equiv \vec{S}'_p(s'_1 + s'_2)^{-1}$; Eq. (1) can be rewritten with the unit magnitude mixing matrix as $\vec{X}_p(t) = C_p(t)[\vec{A}_p(t)]\vec{S}_p(t)$; or explicitly using matrix vector multiplication:

$$\begin{pmatrix} x_1(t) \\ x_2(t) \end{pmatrix} = C_p(t)\begin{bmatrix} a_1 & b_1 \\ a_2 & b_2 \end{bmatrix}\begin{pmatrix} s_1(t) \\ s_2(t) \end{pmatrix} \quad (2)$$

where $a_1 = \cos\theta_a$; $a_2 = \sin\theta_a$ and $b_1 = \cos\theta_b$; $b_2 = \sin\theta_b$. Since the spectral decay factor $C_p(t)$ of an arbitrary pixel p cannot be computed from the first principle due to patients' variable physiques, the unknown tumor depth and thus the intensity should be eliminated by taking the ratio of spectrograms intensities $r_x(t) \equiv x'_1(t)/x'_2(t)$. Moreover, to be further invariant to the imaging environment, the intensity ratio is inverted in terms of sources ratio $\rho_s(t) \equiv s'_1(t)/s'_2(t)$:

$$r_x(t) = \frac{a_1\rho_s(t) + b_1}{a_2\rho_s(t) + b_2}; \quad (3)$$

$$\rho_s(t) = \frac{b_2 r_x(t) - b_1}{-a_2 r_x(t) + a_1}\|\Delta\|^{-1}$$

If the mixing matrix were known, the inversion would be straightforward for a nontrivial determinant of two different unit feature vectors $\|\Delta\| \equiv a_1 b_2 - a_2 b_1 \neq 0$. However, in general, this unknown matrix inversion belongs to an ill-posed class of single-pixel blind source separation which consequently has many possible inverse solutions. Among all of these solutions, one should choose the dynamic equilibrium solution, which, by definition, would be realized most often experimentally.

Two unknown mixing angles of matrix $[A_p]$ of Eq(3) remain to be determined by imposing two physics equilibrium laws:

(1) According to Einstein's theory of photons in a vacuum, light consisting of photons propagates with a constant speed of $c_o$, $\epsilon = \hbar\omega = c_o\hbar k = c_o h/\lambda$, and an increased photon energy $\epsilon_1$ would result in a shortened wavelength $\epsilon_1/\epsilon_2 = \lambda_2/\lambda_1$ inversely linearly proportional to an arbitrary reference state $\epsilon_2$ and $\lambda_2$. However, in a real-world environment, such an energizing phenomenon could not happen in a vacuum and the Einstein formula must be modified according to the medium. In fact, Wien observed[7] early that in Planck's every measurement of the radiation emitted from a blackbody cavity, all the spectral peaks at every equilibrium temperature fall on a linear negative slope, -m, on a log-log plot of the intensity versus the wavelength. This is known as Wien's displacement rule, a power law, shown in FIG. 1:

$$\log \epsilon_1 - \log \epsilon_2 = -m(\log \lambda_1 - \log \lambda_2); \epsilon_1/\epsilon_2 = (\lambda_1/\lambda_2)^{-m}, \quad (4)$$

where $1 > m > 0$ is universal for all blackbody temperatures, which is consistent with Einstein's photon in the vacuum at Wien's power index $m = 1$. Although Wien's index is universal for all blackbody cavity radiators at any temperature, a malignant tumor inside a human body is not as efficient as the ideal cavity radiator and further it cannot exist alone without a feeder source. For example, the infrared (IR) spectrum of a malignant tumor might be calibrated to be a brown body radiator $m = \frac{1}{2}$, that is, $\lambda_1 = \lambda_2(\epsilon_1/\epsilon_2)^{-1/m} = \lambda_2/(\epsilon_1/\epsilon_2)^2$; if the activity energy increases by 40%, a factor about $\epsilon_1 = 1.41\epsilon_2 \cong \sqrt{2}\epsilon_2$, the wavelength will be shortened by a factor 2, shifting from a long IR $\lambda_2$ (8-12 □m) at the ground state $s_2$ toward a mid-IR $\lambda_1$ (3-5 □m) at the excited state $s_1$. The local temperature raises $T_1$-$T_2$ due to the increased energies $\epsilon_1$-$\epsilon_2$ depending on the tumor's specific heat capacity, which can be estimated theoretically by integrating over the spectral density of tumor excited states $s_1$: $n_1 = d\lambda_1/ds_1$ of which each degree of freedom contributes about $K_B T/2$, about 1/80 eV, at a warm room temperature. Nevertheless, such a change is often minutia and imperceptible to the eye; however, a pair of modern satellite cameras can detect the miniscule change by analyzing the dual infrared (IR) spectrograms images. Wien's displacement rule of the spectral peaks of Planck blackbody radiation distribution, see FIG. 1 and Eq. (4), states that hotter sources have their peaks shifted linearly and self-similarly from a long IR regime toward a middle or shorter IR regime. It has been demonstrated that Wien's spectrum shifting rule could be a salient feature of a decrease or increase of angiogenesis effect. Thus, as computed from Eq. (1), the differential slope rule of peak radiation is exactly the finite difference rule:

$$\frac{d(\epsilon_1/\epsilon_2)}{d(\lambda_1/\lambda_2)} = -m(\lambda_1/\lambda_2)^{-m-1} = -m\frac{(\epsilon_1/\epsilon_2)}{(\lambda_1/\lambda_2)} \quad (5)$$

Figure 5:
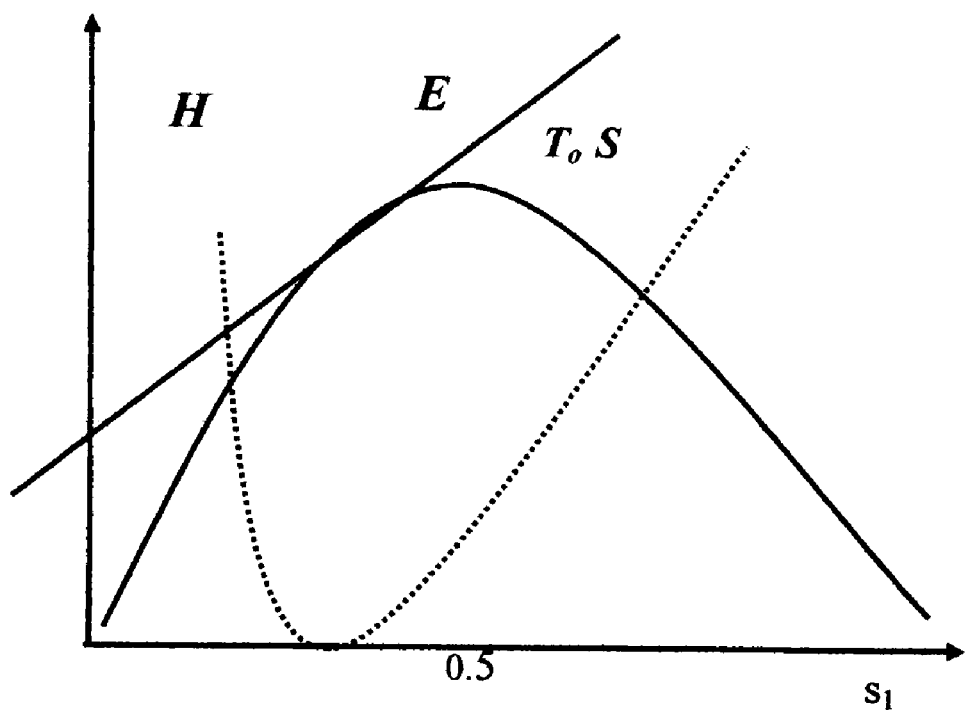
FIG. 5 is a graph plotting the Helmholtz free energy $H=E-T_oS$.

(2) Thermodynamic equilibrium occurs at the real and non-negative Helmholtz free energy at the minimum, $H_p = E_p - T_o S$, illustrated in FIG. 5. In the thermal equilibrium of an open dynamic system at temperature $T_o$, the Helmholtz free energy $H = E - T_o S$ should be at the non-negative minimum of which the approximation linear internal energy E (Taylor expanded near the equilibrium value) can intersect at zero, one, and two points the entropy S which has a simple convex function and maximum at equal source component $s_1 = s_2 = 0.5$. A specific $T_o$ is chosen so that only one intersection provides a unique answer. The single pixel radiation information energy $E_p$ of an open system at a local equilibrium temperature $T_o$ should be subtracted the Shannon-Claudius entropy valid only for a closed-equilibrium system at a maximum entropy: $S/K_B = -s_1 \log s_1 - s_2 \log s_2$ normalized for two component case, $s_2 = 1 - s_1$. It is assumed that the unknown internal energy $E_p$ is analytic and expanded in a Taylor series with respect to the output feature vector $\vec{S}_p$ near the correct inverse solution $\vec{S}^{(o)}_p = [W]_{\alpha\beta} X_\beta$ where the mixing matrix $[A_p]^{-1} = [W]$.

$$H_p = E_{po} + \mu_\alpha(s_\alpha - S^{(o)}_{P\alpha}) + (s_\alpha - S^{(o)}_{P\alpha})\varepsilon_{\alpha\gamma}(s_\gamma - S^{(o)}_{P\gamma}) + \qquad (6)$$
$$K_B T_o \left( \sum_{i=1}^{m} s_i \log s_i + (\mu_o - 1)\left(\sum_{i=1}^{m} s_i - 1\right)\right)$$

where a repeated Greek index for the summation, and $$\mu_i = \left.\frac{\partial E}{\partial s_i}\right|_{s_i = s_i^{(o)}}$$

was the Lagrange constraint, and $$\varepsilon_{ij} = \left.\frac{\partial^2 E}{\partial s_j \partial s_i}\right|_{s_i = s_i^{(o)}} \cong \varepsilon \delta_{ij} \geq 0,$$

an assumed isotropic negative curvature for the convergence. To solve for $s_1$, one computes from the analytical assumption the Taylor series expansion (i) the linear contribution of information radiation energy from Eq. (6) to give the partial differential slope to be exactly equal to a finite difference of the Lagrange components:

$$E_p - E_{po} = \qquad (7)$$
$$\frac{\partial E_p}{\partial s_1}(s_1 - s_1^{(o)}) = [\mu_1 \quad \mu_2]\begin{bmatrix} s_1 - s_1^{(o)} \\ s_2 - s_2^{(o)} \end{bmatrix} = (\mu_1 - \mu_2)(s_1 - s_1^{(o)}); \Rightarrow$$
$$(\mu_1 - \mu_2) = \frac{\partial E}{\partial s_1}$$

where use was made of $s_2^{(o)} \equiv \hat{w}_2^T \vec{X} = 1 - s_1^{(o)}$; (ii) one computes the partial differential of information energy with respect to the malignant source and obtains by the chain rule:

$$\frac{\partial E}{\partial s_1} = \frac{\partial \varepsilon_1/\varepsilon_2}{\partial \lambda_1/\lambda_2} \frac{d\lambda_1/\lambda_2}{ds_1}\bigg|_{s_1 = s_1^{(o)}} = -mn\frac{\varepsilon_1/\varepsilon_2}{\lambda_1/\lambda_2}; \qquad (8)$$

where the wavelength density of the malign states $$n \equiv \frac{d\lambda_1/\lambda_2}{ds_1}\bigg|_{s_1 = s_1^{(o)}}$$

is related to the malignant tissue heat capacity; (iii) the minimum Helmholtz free energy at the isothermal equilibrium. Setting the partial differentiation of H to zero:

$$\frac{\partial H}{\partial s_j} = \mu_j + 2\varepsilon(s_j - s_j^{(o)}) + K_B T_o(\log s_j + 1 + \mu_o - 1) = 0;$$

and imposing the probability percentage normalization $$\sum_{i=1}^{m} s_i = 1$$

to eliminate $\mu_o$. Finally, one obtains, at equilibrium, the solution $s_j = s_j^{(o)} \equiv [W_{j\alpha}]\vec{X}_\alpha$, the McCulloch & Pitts sigmoid logic, similar to artificial neural networks of isothermal brains, $$s_j = \left[1 + \sum_{k=1, k \neq j}^{m} \exp([\mu_j - \mu_k]/K_B T_o)\right]^{-1} \equiv \sigma(\mu_j), \qquad (9)$$

In the two components case, the exact probability formula of the malignance $s_1$ has been derived from Eqs. (7,8,9):

$$s_1 = \left[1 + \exp\left(-mn\frac{\varepsilon_1/\varepsilon_2}{\lambda_1/\lambda_2}\right)\right]^{-1} \qquad (10)$$

The percentage of malignant source is mainly predicted in terms of the measured peak value of mid IR $\epsilon_1$ at the wavelength $\lambda_1$ and the peak of long IR $\epsilon_2$ at $\lambda_2$. Although the universal constant m for a blackbody can approximate our brown body, a realistic value m does not expect to vary appreciable from patient-to-patient. Also, a patient's tissue heat capacity is unlikely to change rapidly, in terms of the density of malignant source $s_1$ with respect to the wavelengths. Even without yet sufficient statistics of measurements, one can already verify the validity of the tumor formula in two limiting cases. (i) The weak source limit: mid IR $\epsilon_1 << \epsilon_2$ yielded $\epsilon_1/\epsilon_2 = 0$ and $s_1 = 0.5$ meaning the malignant tumor has 50% chance, of which the uncertainty can be resolved by subsequent observations further tracking the source ratio over days; (ii) The strong source limit: in the opposite limit $\epsilon_1 >> \epsilon_2$ for strong mid IR and negligible long IR we have the certainty of the malignant tumor $s_1 = 1$.

Figure 6:
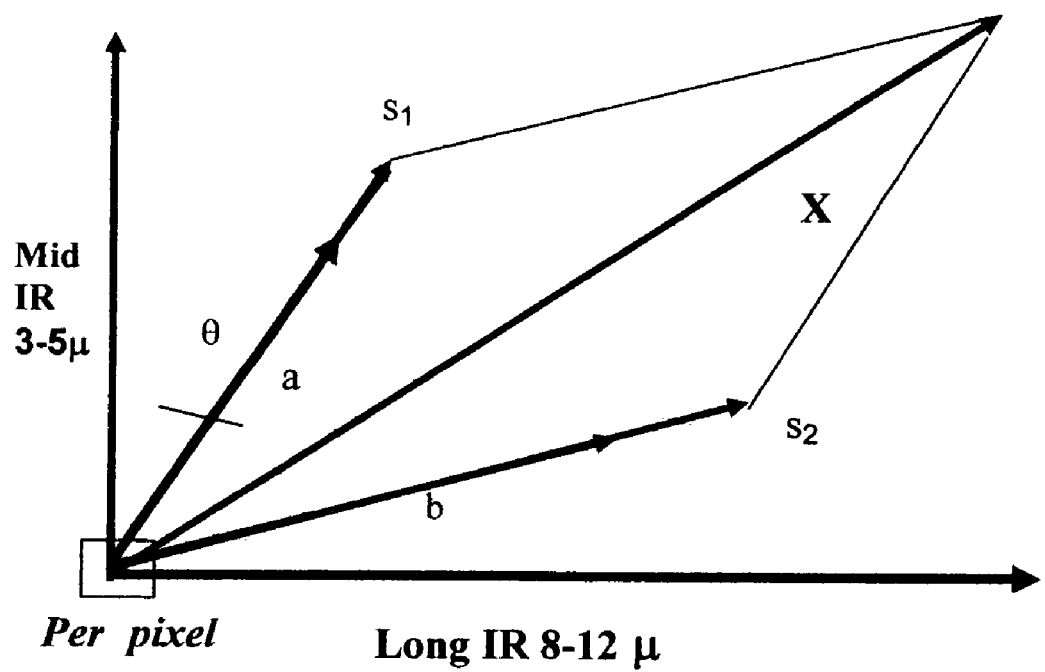
FIG. 6 a vector parallelogram used to determine unknown abnormal spectral features and normal body spectral features.

The minimum H=0 occurs at $E = T_o S$ where the approximation of information radiation energy E intersects at the convex entropy function S at only one point where the mixture temperature $T_o$ was determined, as shown in FIG. 6. Given the percentage of sources $s_1$ & $s_2 = 1 - s_1$, the vector parallelogram can determine those unknown abnormal spectral features and normal body spectral features to be added up to the data vector $\vec{X}$. It is clear that the minimum Helmholtz free energy H=0 implies in a closed system E=0, or, $\epsilon_1/\epsilon_2 = 0$ the maximum Shannon entropy at half chance of malignancy $s_1 = 0.5$ and half chance of benign status $s_2 = 0.5$.

It is determined for $$\frac{\lambda_1}{\lambda_2} \leq 0.5 \text{ and } \frac{\partial \lambda_1}{\partial s_1} \geq \frac{\partial \lambda_2}{\partial s_1},$$

one can experimentally estimate the inverse spectral density of malignant states $$n = \frac{\partial \lambda_1/\lambda_2}{\partial s_1} = \frac{1}{\lambda_2}\left[\frac{\partial \lambda_1}{\partial s_1} - \frac{\lambda_1}{\lambda_2}\frac{\partial \lambda_2}{\partial s_1}\right]_{s_1 = s_1^{(o)}} \approx \frac{1}{\lambda_2}\frac{\partial \lambda_1}{\partial s_1}\bigg|_{s_1 = s_1^{(o)}}$$

Figure 7:
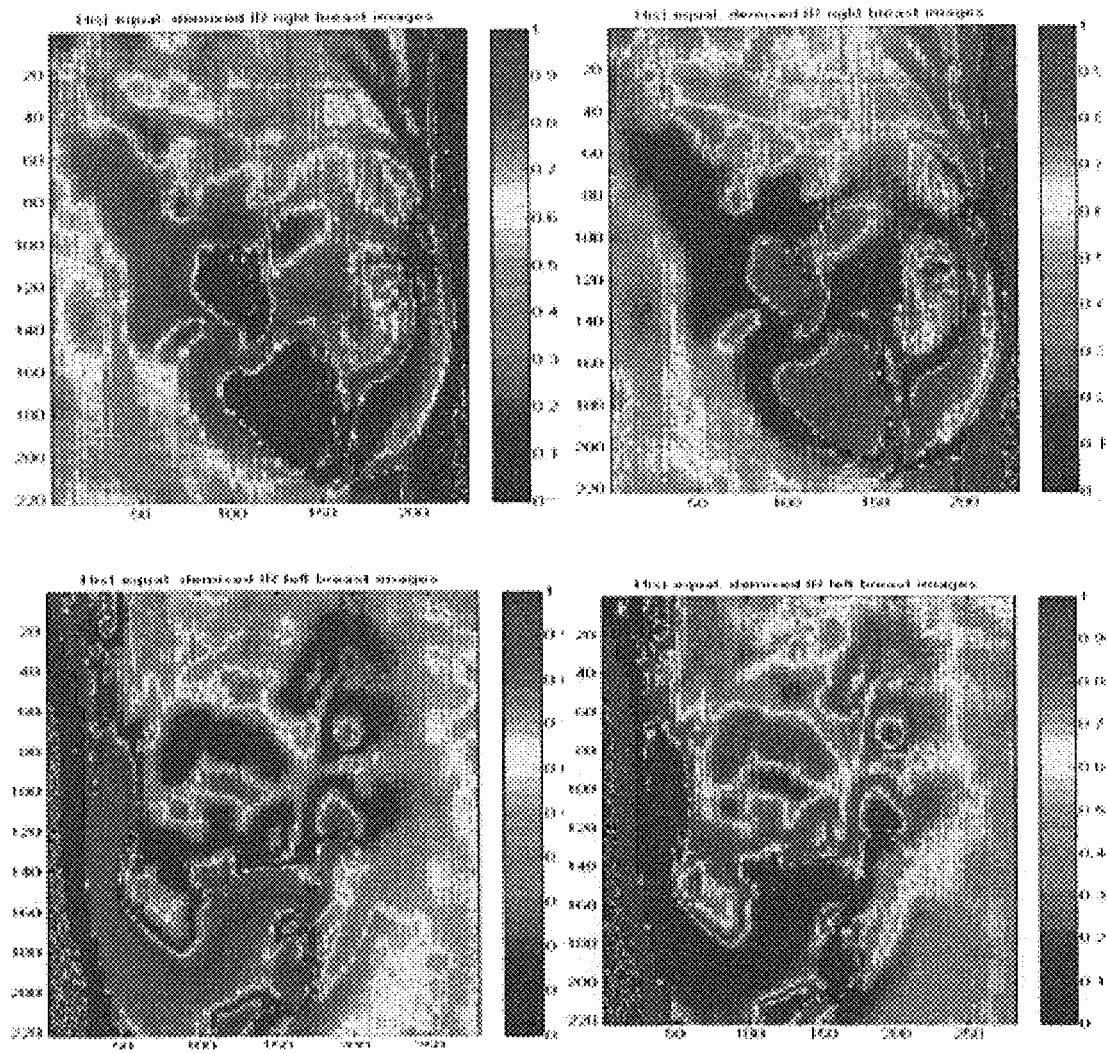
FIG. 7 shows unsupervised classification images of the right breast.

Once the minimum free energy shown in FIG. 5 is used to determine the percentage of malignancy $s_1$, the vector parallelogram shown in FIG. 6 determines the unknown unit feature vectors â,b̂ followed finally by the invariant source ratio $\rho_s(t)$ from Eq. (3). FIG. 7 shows two independent classes discovered with DCIS zero stage near the ring around the right nipple, but not in the left nipple, when the unsupervised classification algorithm (Equations (1) through (10)) was applied to the image of the right breast. Independent classes represented good thermal classes, since most large heat classes came from inside of the breast. The marked area on the right breast indicated the existence of a DCIS of stage #0 (confined) to stage #1 (local spread). When two-color IR spectral-grams were augmented with the help of X-ray based mammography, which could detect microcalcification—areas of cells of a few millimeters or more in diameter, which had been destroyed by cancer. That is, in the unsupervised classification images of the right breast, red means class of high probability (1) and blue means class of low probability (0). The broken ring of small red pixel dots less than millimeter size each and connected right outside quadrant, marked with the cyan circle, sharing the same texture heat supply of shallow capillary blood vessels as the rest but should not be there since the nipple did not usually have the abnormal isolated dotted characteristics unless a stage zero ductile carcinoma in situ (DCIS) is present. This dual band infrared image serves as merely a telemedicine super-resolution decision aid to doctors, which would require an intelligent data basis tracking over months or at least weeks to be ascertained by other intrusive means. Independent classes represent usual thermal diffusion Gaussian classes since most large heat classes come from the normal blood vessels of the breast. It has been derived for an open system that this generalized information theory, min H, could capture both neural network sigmoid logic as open dynamic system isothermal partition function and also the Hebbian unsupervised learning rules, $\Delta[W_{ij}] = X_i \mu_j$. Given input data, the output is not a desired output, rather the internal Lagrange variable, whose sigmoid squashed output was the desired feature vector. By the dimensionality analysis, the synaptic weights were volts mediated by mini-volts neuro-transmittents and then for the physical power energy the internal Lagrange variable must be amperes representing the dendrite ion channel pico-amperes mediated by housekeeping glial cells. Two passive IR spectrum image data $\vec{X}_p(t)$ the unknown feature vector $\vec{S}_p(t)$ was extracted without external teachers, as the percentage of mid IR band versus long IR band in proportion to malignant versus benign tumors. This passive tracking of tumor-shrinkage by spectrograms might reduce the check-up frequency of X-ray mammograms.

Figure 2:
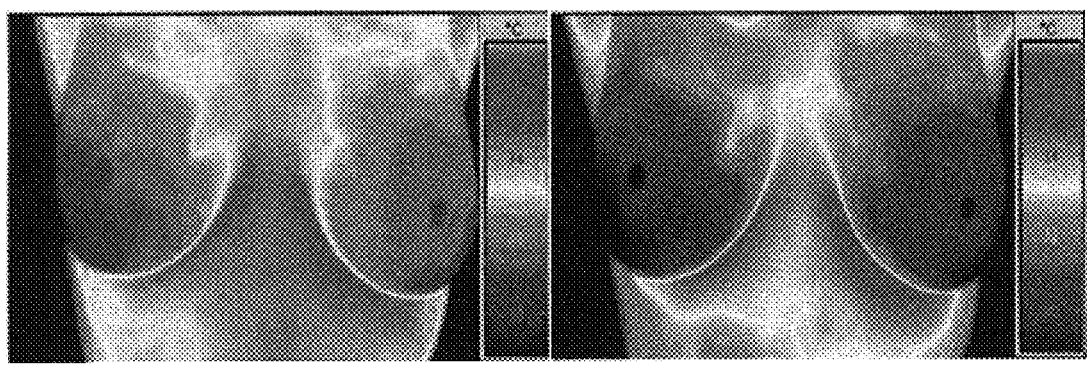
FIG. 2 shows a conventional breast cancer diagnosis spectrogram for a healthy patient.

Several remarks are in order: the study was perfromed (i) to gain the confidence in dual use of military ATR technology to public health, before many more resources were committed for comprehensive controlled studies in terms of the ROC. The study was done with volunteer patients under auxiliary passively IR spectral-grams imaging during their return visits for drug chemotherapy treatments; (ii) during treatment, the passive IR spectral-grams might provide doctors or caretakers a real-time insight for prescribing an appropriate chemotherapy dosage; and (iii) to reduce hospital return checkup frequency with a potential detection of any deadly recurrence of cancer here and elsewhere after the initial recovery. It would be beneficial to supplement that active mammogram imaging with more frequently passive IR spectrograms in-between the hospital treatment and checkups. (iv) The final sequence was animated in a time-reverse video to document the getting-better-to-complete-recovery history, which, when played backward, simulates a video of a high-risk patient getting sick as an earliest possible detection by passive spectrograms. When the predictions of these two spectrograms images were compared with the oncologist prognoses, the results consistently gave us the confidence of unsupervised ATR performance with IR dual spectrograms. Of course, the physiology change of getting better is different than that of getting sick, but the utility of IR dual spectrograms for passive screening is advantageous. (v) Modern satellite imaging is more reliable, and is passive in order to be stealthy, which qualities are suitable for screening public health status because it is a non-intrusive procedure. However, ordinarily satellite cameras are precision instruments operated cryogenically using liquid nitrogen coolant in seven or more spectrum color bands (from visible light to invisible IR) and require a supercomputer for processing. According to the present invention, the dual IR spectrograms reduced the number of satellite cameras to two cameras. Resulting spectral images are analyzed with a personal computer having an unsupervised classifier, to automatically extract the necessary features without the inconvenience of an expert-in-the-loop to adjust the threshold. In this preliminary study, commercial-off-the-self (COTS) spectral cameras were adopted. Initially, blind-controlled studies of a healthy 10,000 but risky 1% patients over several years were avoided in order to plot the results in terms of the Receiver Operation Characteristics (ROC) of the probability of detection of 100 sickness incidents versus the false negative rate. Rather than relying on the total intensity thermographs and its associated variation over time, as shown in FIGS. 2 and 3, applications in multi-spectral remote sensing on Landast seven multispectral band images were demonstrated. The unsupervised classification method described in Equations (1) through (10) were demonstrated to be capable of discovering small man-made objects located sparsely in a desert when the objects exhibit similarly-shaped spectral intensities as they would if located in a city area. According to the present invention, results of the same algorithm were shown to apply to unsupervised classification of the multi-spectral IR breast images for early breast cancer detection and tracking. Moreover, the design of the present invention enables satellite-precision cameras to be affordable and portable, not only for hospitals, but also for laboratory and household use. An electrically cooled dual-spectrum IR camera using an optically co-axial unit-frame is provided according to a biomimetic fovea. The imaging backplane houses both the long IR wavelength Charged Coupled Device (CCD) and a single quantum detector capability at the mid-IR wavelength in terms of one dimensional (1-D) Carbon Nanotubes (CNT)

per pixel, which has a minimum occlusion about a nano-size in front of the CCD. The 1-D nature of CNT produces a reduced thermal noise, about ½ $K_BT$ compared to 3/2 $K_BT$. Thus, electrical diffusion cooling preferably is used rather than liquid nitrogen to keep a steady backplane environment to maintain the minimum resolvable temperature difference (MRTD) similar to that of cryogenic mid-IR camera, about 0.02 degree Kelvin.

A nano-robot can be used to assemble one-dimmensional quantum mechanical band-gap material, such as carbon nanotube, at the back-plane. For example, see U.S. Pat. No. 6,862,924 to Ning Xi as an example of a device used for such nanomanipulation. The middle infrared detectors are designed to be located above the long infrared CCD, which uses the x-y plane row-sum column-sum read-out.

This architecture is similar to that of a human visual retina, which detects blue in front, green in the middle, and red behind, but read out along the z-direction. Similar to human eyes, the detector has almost single-photon detection capability using a Wheatstone bridge with 4-armed balanced circuitry to read out along z-direction pixel-by-pixel, which in turn drives an electrical current provided by a battery only when one or two of the arms, made of carbon nanotubes, receive middle infrared photons and break the balance.

Figure 8:
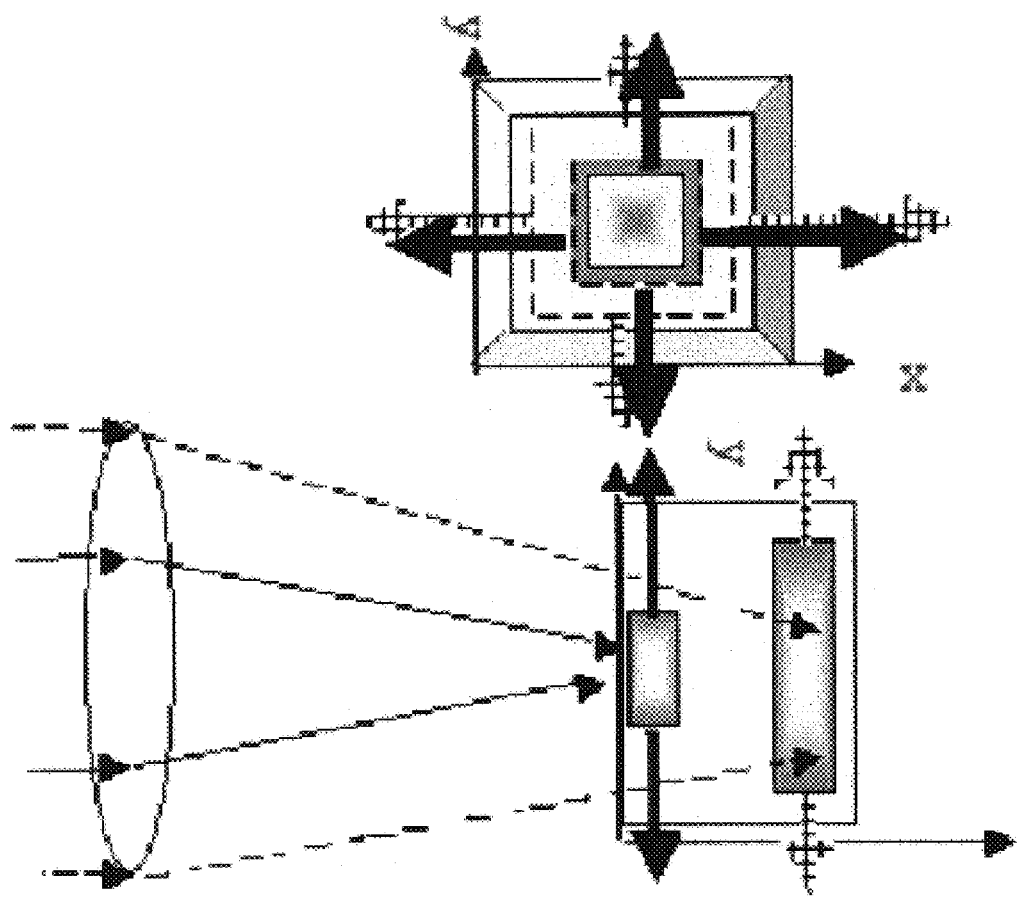
FIG. 8 shows an example of a two-spectrum fovea design for a 3-D FPA.

Thus, the multi-spectral camera shares co-axially identical infrared optic lenses which focus naturally at multiple focal planes for different spectral wavelengths, similar to a multi-color fovea architecture. This is possible without usual color filter loss, because the 1-D quantum detector carbon nanotube (CNT) is on the order of 1 nanometer in diameter, which has a minimum occlusion of less than 1% from other radiation detectors and each can orthogonal to the other and selectively tuned for different spectral wavelengths. For example, two layers preferably consist of one mid-IR at 3 to 5 micron wavelengths and the other at a longer optical path provided by a standard un-cooled long-IR Focal Plane Array (FPA) with an intercept at 8 to 12 micron wavelengths. FIG. 8 shows an example of a two-spectrum fovea design for a 3-D FPA. The front FPA is carbon nanotube 1-D quantum detector for mid-IR wavelengths, and the back FPA is standard un-cooled CCD device for long-IR imaging. As shown in FIG. 8, in the architecture of the fovea design without filter loss, the occlusion of the CNT for long IR is less than 1%.

Figure 9:
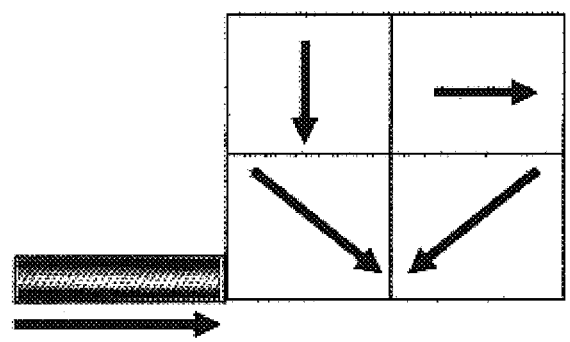
FIG. 9 shows unit cells of 2×2 pixels covering four orthogonal polarizations along a 1-D CNT.
Figure 10:
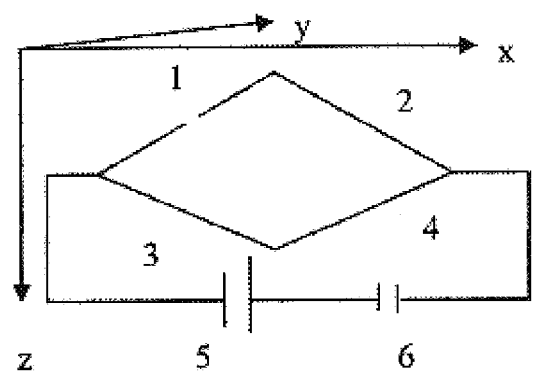
FIG. 10 shows a Wheatstone bridge balance circuit.

Orthogonal polarizations are arranged in a 2×2 pixels as shown in FIG. 9. FIG. 9 shows that unit cells of 2×2 pixels cover four orthogonal polarizations along a 1-D CNT for the electrical field direction. In addition, each pixel can detect a single photon by monitoring the balance of a Wheatstone bridge circuit, as shown in FIG. 10. As shown, a single-pixel single-photon read out by fovea cone single photon detector logic "negate the converse" implemented circuit, for example, a Wheatstone bridge balance circuit, is used per pixel. In the figure, (1) a band gap CNT is exposed on the x-y plane in a specific polarization direction; (2)-(3)-(4) a conductor CNT is in balance when no impinging photons are present; (5) a gain biased voltage is provided; and (6) a capacitor is provided for charge accumulation read-out along the z-axis. Thus, room temperature or non-cryogenic operation is possible for single-photon signal-to-noise ratio (SNR).

Figure 11:
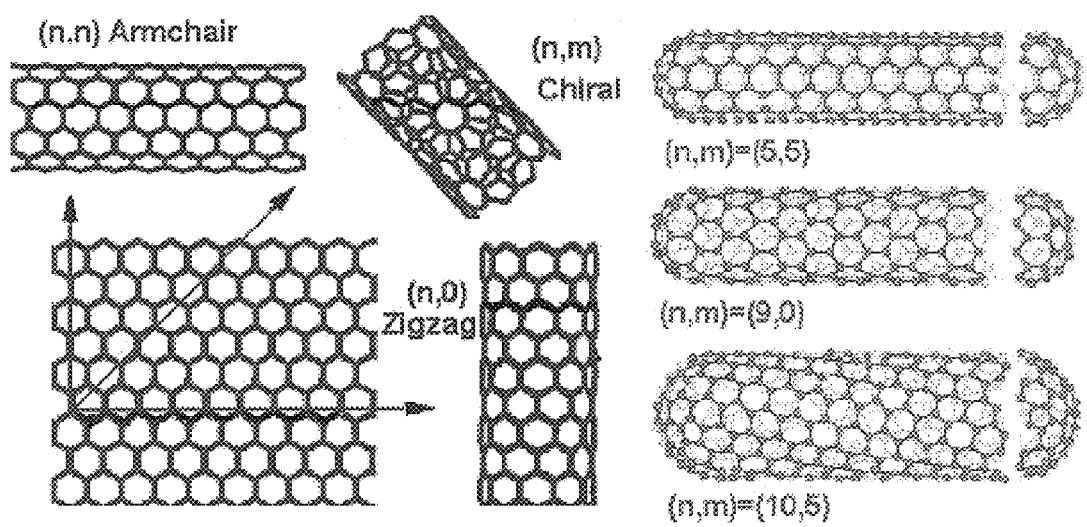
FIG. 11 shows different categories of carbon nanotubes.

There are two types of CNT: conductors and semiconductors. Nano-robotic assembly is possible at specific orientations and locations. For example, as shown in FIG. 11, two major categories of CNT include the one-dimensional quantum conductor known as the Armchair (n=m are CNT unit cell two chiral vectors); and band-gap semiconductors called Zigzag (n=0 or m=0 without being divisible by 3). Further, there are single-wall CNTs and multi-wall CNTs.

In general, a signal of 1000 to 100 photons provides statistically stable data, and therefore the usual SNR factor of 5 orders of magnitude is achieved at non-cryogenic cooling or room temperature operation. This is estimated as follows:

CNT bandgap at Mid IR 3 to 5 micrometer
Signal photon $$\Delta E = \hbar\omega = h\frac{c}{\lambda} = 0.414 \text{ eV} \Leftrightarrow 0.248 \text{ eV}$$

Between room temperature T=300° K; Liquid Nitrogen T=77° K
Gaussian noise energy $$K_BT = \frac{1}{40} \text{ eV} = 0.025 \text{ eV}; 0.006 \text{ eV}$$

Johnson shot noise whose mean = variance

1D: $\frac{1}{2}K_BT$ < dark current < 3D: $\frac{3}{2}K_BT$ at room temperature 0.0125 eV < dark current < 0.0375 eV $$SNR_{room} = \frac{0.4 \Leftrightarrow 0.2}{0.01} = 40 \Leftrightarrow 20 \text{ if 1-}D$$

(otherwise: 13 $\Leftrightarrow$ 7 for 3-$D$)

at 77° K $\Rightarrow$ noise $0.006 \times 3/2 \cong 0.01$ (1% eV)

$$SNR_{cryogenic} = \frac{0.4 \Leftrightarrow 0.2}{0.01} = 40 \Leftrightarrow 20 \text{ if 3-}D$$

Figure 12:
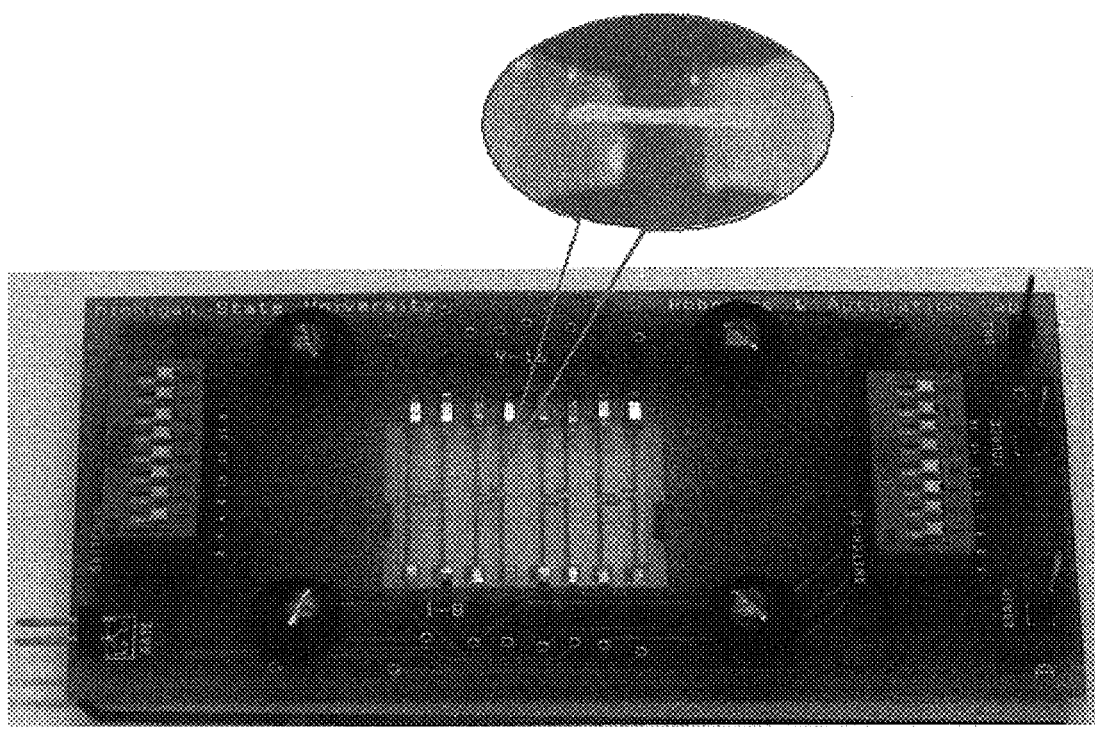
FIG. 12 shows a carbon nanotube-based IR detector array.

FIG. 12 shows a carbon nanotube-based IR detector array. In the array array, each pixel includes a multi-walled carbon nanotube with a properly tuned bandgap for detection of a selected infrared spectrum.

A nano-robot can assemble one-dimensional quantum mechanical bandgap material such as a carbon nanotube at the backplane. Preferably, this is designed to be above the long infrared charge coupled device (CCD), which uses the x-y plane row-sum column-sum readout.

Particular exemplary embodiments of the present invention have been described in detail. These exemplary embodiments are illustrative of the inventive concept recited in the appended claims, and are not limiting of the scope or spirit of the present invention as contemplated by the inventor.

I claim:

1. A process of performing a medical test, comprising:
   taking multi-spectral images of an area of interest of a patient;
   wherein taking multispectral images includes taking images using a dual-spectrum infrared camera;
   wherein the dual-spectrum infrared camera includes a long-infrared wavelength detector and a mid-infrared wavelength detector;
   wherein the mid-infrared wavelength detector includes a detector array having carbon nanotubes; and
   wherein the carbon nanotubes are tuned-bandgap carbon nanotubes.

2. The process of claim 1, wherein taking multi-spectral images includes taking substantially simultaneous images of the area of interest using a plurality of cameras, wherein each of the cameras provides an image in respective different spectra.

3. The process of claim 1, wherein the cameras are infrared cameras.

4. The process of claim 1, wherein the spectra are infrared spectra.

5. The process of claim 1, wherein the plurality of cameras are two cameras.

6. The process of claim 1, wherein the carbon nanotubes are detector elements.

7. The process of claim 1, wherein each pixel of resolution of the detector array includes a balanced Wheatstone bridge circuit including one of the tuned-bandgap carbon nanotubes.

8. A process of performing a medical diagnosis, comprising:
performing a medical test according to claim 1;
comparing the images to spectrograms of subjects having a known health issue; and
diagnosing a health status of the patient based on a correlation of the images to the spectrograms.

9. A process of performing a medical prognosis, comprising:
performing a medical test according to claim 1, wherein the patient has a known health issue of a particular type;
comparing the images to spectrograms of subjects having the known health issue of the particular type; and
providing a prognosis for the patient based on a correlation of the images to the spectrograms.

10. A process of performing a medical test, comprising:
taking multi-spectral images of an area of interest of a patient;
wherein taking multispectral images includes taking images using a multiple-spectrum camera;
wherein the multiple-spectrum camera is a dual-spectrum camera; and
wherein the multiple-spectrum camera is cooled by electrical dissipation.

11. The process of claim 10, wherein the multiple-spectrum camera is a dual-spectrum infrared camera.

12. The process of claim 11, wherein the dual-spectrum infrared camera includes any two of a long-infrared wavelength detector, a mid-infrared wavelength detector, and a short-infrared wavelength detector.

13. The process of claim 12, wherein the dual-spectrum infrared camera includes a long-infrared wavelength detector and a mid-infrared wavelength detector.

14. The process of claim 13, wherein the mid-infrared wavelength detector includes a detector array having carbon nanotubes.

15. The process of claim 14, wherein the carbon nanotubes are detector elements.

16. The process of claim 10, wherein taking multi-spectral images includes taking substantially simultaneous images of the area of interest using a plurality of cameras, wherein each of the cameras provides an image in respective different spectra.

17. The process of claim 16, wherein the cameras are infrared cameras.

18. The process of claim 16, wherein the spectra are infrared spectra.

19. The process of claim 16, wherein the plurality of cameras are two cameras.

20. A process of performing a medical diagnosis, comprising:
performing a medical test according to claim 10;
comparing the images to spectrograms of subjects having a known health issue; and
diagnosing a health status of the patient based on a correlation of the images to the spectrograms.

21. A process of performing a medical prognosis, comprising:
performing a medical test according to claim 10, wherein the patient has a known health issue of a particular type;
comparing the images to spectrograms of subjects having the known health issue of the particular type; and
providing a prognosis for the patient based on a correlation of the images to the spectrograms.

22. A process of performing a medical test, comprising:
taking multi-spectral images of an area of interest of a patient;
wherein taking multispectral images includes taking images using a multiple-spectrum camera;
wherein the multiple-spectrum camera is a dual-spectrum camera; and
wherein the multiple-spectrum camera is cooled by refrigeration.

23. The process of claim 22, wherein the multiple-spectrum camera is a dual-spectrum infrared camera.

24. The process of claim 23, wherein the dual-spectrum infrared camera includes any two of a long-infrared wavelength detector, a mid-infrared wavelength detector, and a short-infrared wavelength detector.

25. The process of claim 24, wherein the dual-spectrum infrared camera includes a long-infrared wavelength detector and a mid-infrared wavelength detector.

26. The process of claim 25, wherein the mid-infrared wavelength detector includes a detector array having carbon nanotubes.

27. The process of claim 26, wherein the carbon nanotubes are detector elements.

28. The process of claim 22, wherein taking multi-spectral images includes taking substantially simultaneous images of the area of interest using a plurality of cameras, wherein each of the cameras provides an image in respective different spectra.

29. The process of claim 28, wherein the cameras are infrared cameras.

30. The process of claim 28, wherein the spectra are infrared spectra.

31. The process of claim 28, wherein the plurality of cameras are two cameras.

32. A process of performing a medical diagnosis, comprising:
performing a medical test according to claim 22;
comparing the images to spectrograms of subjects having a known health issue; and
diagnosing a health status of the patient based on a correlation of the images to the spectrograms.

33. A process of performing a medical prognosis, comprising:
performing a medical test according to claim 22, wherein the patient has a known health issue of a particular type;
comparing the images to spectrograms of subjects having the known health issue of the particular type; and
providing a prognosis for the patient based on a correlation of the images to the spectrograms.

34. A process of performing a medical test, comprising:
taking multi-spectral images of an area of interest of a patient;

wherein taking multispectral images includes taking images using a multiple-spectrum camera;
wherein the multiple-spectrum camera is a dual-spectrum camera; and
wherein the multiple-spectrum camera includes a backplane, further comprising refrigerating the backplane.

35. The process of claim 34, wherein the multiple-spectrum camera is a dual-spectrum infrared camera.

36. The process of claim 35, wherein the dual-spectrum infrared camera includes any two of a long-infrared wavelength detector, a mid-infrared wavelength detector, and a short-infrared wavelength detector.

37. The process of claim 36, wherein the dual-spectrum infrared camera includes a long-infrared wavelength detector and a mid-infrared wavelength detector.

38. The process of claim 37, wherein the mid-infrared wavelength detector includes a detector array having carbon nanotubes.

39. The process of claim 38, wherein the carbon nanotubes are detector elements.

40. The process of claim 34, wherein taking multi-spectral images includes taking substantially simultaneous images of the area of interest using a plurality of cameras, wherein each of the cameras provides an image in respective different spectra.

41. The process of claim 40, wherein the cameras are infrared cameras.

42. The process of claim 40, wherein the spectra are infrared spectra.

43. The process of claim 40, wherein the plurality of cameras are two cameras.

44. A process of performing a medical diagnosis, comprising:
performing a medical test according to claim 34;
comparing the images to spectrograms of subjects having a known health issue; and
diagnosing a health status of the patient based on a correlation of the images to the spectrograms.

45. A process of performing a medical prognosis, comprising:
performing a medical test according to claim 34, wherein the patient has a known health issue of a particular type;
comparing the images to spectrograms of subjects having the known health issue of the particular type; and
providing a prognosis for the patient based on a correlation of the images to the spectrograms.

46. A process of performing a medical test, comprising:
taking multi-spectral images of an area of interest of a patient;
wherein taking multispectral images includes taking images using a multiple-spectrum camera;
wherein the multiple-spectrum camera is a dual-spectrum camera; and
further comprising cryogenically cooling the multiple-spectrum camera.

47. The process of claim 46, wherein cryogenically cooling the multiple-spectrum camera includes using liquid nitrogen as a coolant.

48. The process of claim 46, wherein the multiple-spectrum camera is a dual-spectrum infrared camera.

49. The process of claim 48, wherein the dual-spectrum infrared camera includes any two of a long-infrared wavelength detector, a mid-infrared wavelength detector, and a short-infrared wavelength detector.

50. The process of claim 49, wherein the dual-spectrum infrared camera includes a long-infrared wavelength detector and a mid-infrared wavelength detector.

51. The process of claim 50, wherein the mid-infrared wavelength detector includes a detector array having carbon nanotubes.

52. The process of claim 51, wherein the carbon nanotubes are detector elements.

53. The process of claim 46, wherein taking multi-spectral images includes taking substantially simultaneous images of the area of interest using a plurality of cameras, wherein each of the cameras provides an image in respective different spectra.

54. The process of claim 53, wherein the cameras are infrared cameras.

55. The process of claim 53, wherein the spectra are infrared spectra.

56. The process of claim 53, wherein the plurality of cameras are two cameras.

57. A process of performing a medical diagnosis, comprising:
performing a medical test according to claim 46;
comparing the images to spectrograms of subjects having a known health issue; and
diagnosing a health status of the patient based on a correlation of the images to the spectrograms.

58. A process of performing a medical prognosis, comprising:
performing a medical test according to claim 46, wherein the patient has a known health issue of a particular type;
comparing the images to spectrograms of subjects having the known health issue of the particular type; and
providing a prognosis for the patient based on a correlation of the images to the spectrograms.

59. A multi-spectral camera, comprising:
a long-infrared charge-coupled device;
a mid-infrared detector array; and
a control device that synchronizes operation of the charge-coupled device and the detector array;
wherein the mid-infrared detector array includes carbon nanotubes; and
wherein the carbon nanotubes are tuned-bandgap carbon nanotubes.

60. The multi-spectral camera of claim 59, wherein the carbon nanotubes are detector elements.

61. The multi-spectral camera of claim 59, wherein each pixel of resolution of the detector array includes a balanced Wheatstone bridge circuit including one of the tuned-bandgap carbon nanotubes.

62. The multi-spectral camera of claim 61, wherein adjacent pixels of the detector array are arranged for orthogonal polarization.

63. The multi-spectral camera of claim 59, wherein the charge-coupled device and the detector array are co-axially aligned.

64. A multi-spectral camera, comprising:
a long-infrared charge-coupled device;
a mid-infrared detector array;
a control device that synchronizes operation of the charge-coupled device and the detector array; and
conductive members that cool the detector array by dissipation.

65. The multi-spectral camera of claim 64, wherein the mid-infrared detector array includes carbon nanotubes.

66. The multi-spectral camera of claim 65, wherein the carbon nanotubes are detector elements.

67. The multi-spectral camera of claim 64, wherein the charge-coupled device and the detector array are co-axially aligned.

68. A multi-spectral camera, comprising:
a long-infrared charge-coupled device;
a mid-infrared detector array;
a control device that synchronizes operation of the charge-coupled device and the detector array; and
a refrigeration element that cools the detector array.

69. The multi-spectral camera of claim 68, wherein the mid-infrared detector array includes carbon nanotubes.

70. The multi-spectral camera of claim 69, wherein the carbon nanotubes are detector elements.

71. The multi-spectral camera of claim 68, wherein the charge-coupled device and the detector array are co-axially aligned.

72. A multi-spectral camera, comprising:
a long-infrared charge-coupled device;
a mid-infrared detector array;
a control device that synchronizes operation of the charge-coupled device and the detector array; and
a cryogenic cooling element that cools the detector array.

73. The multi-spectral camera of claim 72, wherein the cryogenic cooling element uses liquid nitrogen as a coolant.

74. The multi-spectral camera of claim 72, wherein the mid-infrared detector array includes carbon nanotubes.

75. The multi-spectral camera of claim 74, wherein the carbon nanotubes are detector elements.

76. The multi-spectral camera of claim 72, wherein the charge-coupled device and the detector array are co-axially aligned.

* * * * *